United States Patent [19]

Togasaki

[11] Patent Number: 5,788,971
[45] Date of Patent: Aug. 4, 1998

[54] ACTIVE OXYGEN FREE RADICAL SCAVENGING AGENT

[75] Inventor: Keiichi Togasaki, Osaka, Japan

[73] Assignee: Sky. Food Co., Ltd., Osaka, Japan

[21] Appl. No.: 367,277

[22] PCT Filed: Oct. 21, 1993

[86] PCT No.: PCT/JP93/01524

§ 371 Date: Jan. 11, 1995

§ 102(e) Date: Jan. 11, 1995

[51] Int. Cl.$^6$ .............................. A61K 35/78; A23L 1/303
[52] U.S. Cl. ..................... 424/195.1; 426/430; 426/542; 426/544; 426/655
[58] Field of Search ................... 424/195.1; 426/430, 426/655, 542, 544

[56] References Cited

U.S. PATENT DOCUMENTS 4,387,110  6/1983  Emmi et al. ........................ 426/430

FOREIGN PATENT DOCUMENTS 59-45385   3/1984  Japan.
64-25726   1/1989  Japan.
3-221587   9/1991  Japan.

OTHER PUBLICATIONS

"Free Radicals and Medicines in Japan and China" by Kokusai Isho Shuppan.

*Primary Examiner*—Herbert J. Lilling
*Attorney, Agent, or Firm*—Davis and Bujold

[57] ABSTRACT

An active oxygen free radical scavenging agent superior in scavenging active oxygen free radicals produced in organisms is provided. The active oxygen free radical extinguishing agent includes green tea leaf extract containing epigallo catechin gallate and sunflower seed extract containing chlorogenic acid. When administrating green tea leaf extract and sunflower seed extract simultaneously as disclosed in the embodiment, the active oxygen free radical scavenging effect greatly excels the same when said two kinds of active oxygen free radical scavenging agents are separately administrated as shown in reference 2 and reference 3, or the same when rhubarb is administrated as shown in reference 4.

9 Claims, 1 Drawing Sheet

ACTIVE OXYGEN FREE RADICAL SCAVENGING AGENT

TECHNICAL FIELD

This invention relates to active oxygen free radical scavenging agent for scavenging active oxygen free radicals produced in the process of metabolizing in organisms.

BACKGROUND ART

Active oxygen free radicals produced in organisms are known to attack nucleic acid, protein, nucleotide, amino acid, sugar, organic acid, etc. They are also known to have significant relationships to inflammation, cerebral hemorrhage, arterial sclerosis, generation of cancers, destroying or weakening of cancers, radiation damage, cataract, aging, etc.

For scavenging such active oxygen free radicals, rhubarb, i.e. Chinese GAOU is effective as an active oxygen free radical scavenging agent according to "Free Radicals and Medicines in Japan and China" published by KOKUSAI ISHO SHUPPAN. Catechin extracted from green tea leaves also has an effect to scavenge active oxygen free radicals according to "Fragrance J." published by Fragrance Journal.

Those conventionally developed active oxygen free radical scavenging agents could not perfectly prevent generation of cancers, etc., for they were not effective enough to scavenge active oxygen free radicals produced in organisms.

DISCLOSURE OF INVENTION

Wherefore, an object of this invention is to provide an active oxygen free radical scavenging agent for scavenging active oxygen free radicals produced in organisms effectively.

To attain this object, the present invention provides an active oxygen free radical scavenging agent including green tea leaf extract containing epigallo catechin gallate and sunflower seed extract containing chlorogenic acid.

As a result of measuring active oxygen free radical scavenging effects with various chemical products, the applicant discovered that sunflower seed extract has an effect to scavenge active oxygen free radicals.

Furthermore, the measurement revealed that the active oxygen free radical scavenging effect when administrating green tea leaf extract containing epigallo catechin gallate and sunflower seed extract simultaneously greatly excels the same when the two kinds of extracts are separately administrated.

The active oxygen free radical scavenging agent according to the present invention effectively scavenges active oxygen free radicals, for it includes green tea leaf extract containing epigallo catechin gallate and sunflower seed extract containing chlorogenic acid.

The mixing amounts of green tea leaf extract and sunflower seed extract are, for example when these extracts are dispersed in water, both preferably from 0.01 weight per cent to 10.00 weight per cent. In addition, antioxidants such as ascorbic acid, vitamin E and beta carotene, and fragrances, etc., may be included in the agent.

For dispersing the above extracts, substances such as xanthum gum, Guar gum, carboxymethyl cellulose, saponin, fatty acid esters and soybean protein are added and dispersed with the conventional type of homogenizer.

When manufacturing the agent in solid or powdered form, the amounts of each extracts are selected at will. As being dispersed in water, antioxidants such as ascorbic acid, vitamin E and beta carotene, fragrances, etc., may be included. Various methods such as mixing with lactose, dextrin, food material, etc. before dispersing is applicable.

BEST MODE FOR CARRYING OUT THE INVENTION

Figure 1:
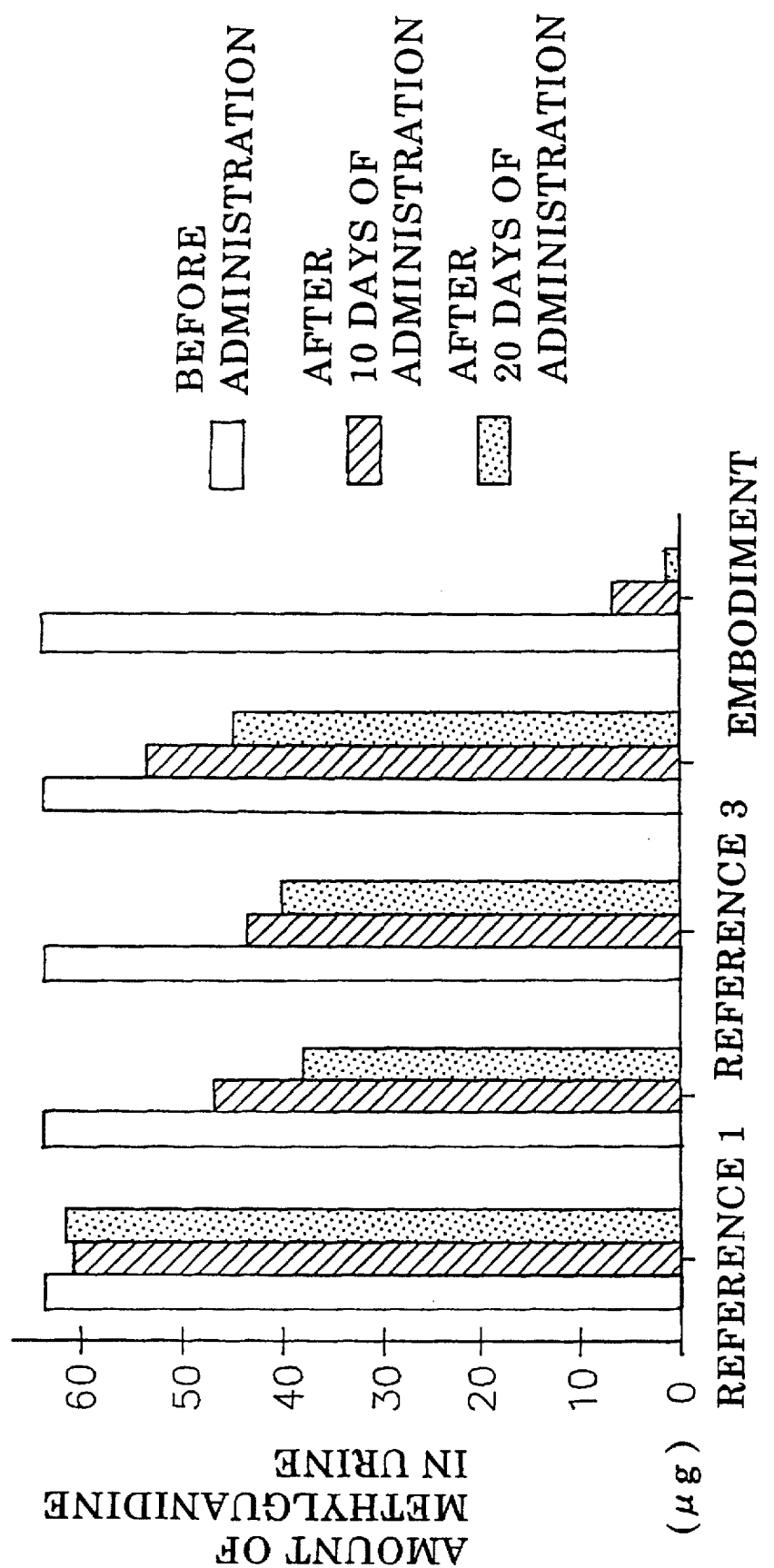
FIG. 1 is a graphs which shows the effect of the active oxygen free radical scavenging agent embodying the present invention.

The embodiment of the invention is now explained referring to the drawing FIGURE.

In an organism seized with renal failure, active oxygen free radical, mentioned free radical hereafter, especially hydroxyradical, acts to produce methylguanidine from creatine existing in muscles of vertebrates. Therefore, according to "Free Radicals and Medicines in Japan and China" published by KOKUSAI ISHO SHUPPAN, a research shows that by measuring the amount of methylguanidine in urine of animals seized with renal failure, the amount of hydroxyradical existing in the organism is estimated.

Based on the above research, the applicant measured the effect of the present invention in feeding test in which the amount of methylguanidine in urine of rats seized with renal failure is measured. The animals used in the test were seven Wister rats of 7 ages in week seized with renal failure as a result of oral administration of diet containing 0.5% of adenine for 4 weeks. During the experiment, the following active oxygen free radical scavenging agents are orally administrated with basal diet to the above rats seized with renal failure, and the changes of the amounts of the methylguanidine in urine were observed.

Embodiment: 15 mg per day of green tea leaf extract and 15 mg per day of sunflower seed extract Reference 1: basal diet alone Reference 2: 30 mg per day of green tea leaf extract Reference 3: 30 mg per day of sunflower seed extract Reference 4: 30 mg per day of aqueous rhubarb extract The green tea leaf extract is produced by filtering and powdering Japanese green tea leaves after extracting with ethyl acetate. Ninety-eight per cent of the green tea leaf extract is solid material, in which the main component is epigallo catechin gallate and the remaining component is not clarified.

The sunflower seed extract is generally known as antioxidant, for example HERIANT manufactured by DAINIPPON INKI Co., Ltd., in which the main component is chlorogenic acid.

FIG. 1 shows the changes of the amounts of methylguanidine in urine of the rats seized with renal failure during continuous administrating of the active oxygen free radical scavenging agents for 10 days or 20 days. As shown in FIG. 1, in reference 2, 3, and 4, the amounts of methylguanidine in urine of the rats during administration of active oxygen free radical scavenging agents decreases from 60 µg to 35–45 µg during 20 days. This proves that green tea leaf extract, sunflower seed extract and aqueous rhubarb extract are respectively effective in scavenging active oxygen free radicals. However, the effects of those active oxygen free radical scavenging agents are relatively weak.

On the contrary, in the embodiment, the amounts of methylguanidine in urine of rats administrated the active oxygen free radical scavenging agents decreases rapidly and disappears almost perfectly after 20 days of continuous administration. This shows that by administrating active oxygen free radical scavenging agents containing green tea leaf extract and sunflower seed extract disclosed in the embodiment, the free radicals existing in organisms are almost perfectly scavenged. Furthermore, by administrating active oxygen free radical scavenging agents disclosed in the embodiment containing green tea leaf extract and sunflower seed extract for 20 days, uremia, which is a clinical symptom of renal failure, is remarkably relieved.

Accordingly, the active oxygen free radical scavenging agent of the present invention is effective in scavenging active oxygen free radicals which may cause inflammation, cerebral hemorrhage, arterial sclerosis, generation of cancers, radiation damage, cataract, aging, etc.

Furthermore, as compared with rhubarb whose usage is limited to drugs, the active oxygen free radical scavenging agent of the present invention is used as following natural food additives. Therefore, it is used in extremely broad industrial fields.

For example, active oxygen free radical scavenging drinks containing the ingredients of applications 1–3 are preferably manufactured.

| Application 1: | |
| --- | --- |
| green tea leaf extract | 5 weight % |
| sunflower seed extract | 2 weight % |
| beta carotene oil | 0.01 weight % |
| fatty acid ester as dispersing agent | 1 weight % |
| water | 91.99 weight % |
| Application 2: | |
| green tea leaf extract | 5 weight % |
| sunflower seed extract | 2 weight % |
| beta carotene oil | 0.01 weight % |
| ascorbic acid | 1 weight % |
| fatty acid ester as dispersing agent | 1 weight % |
| water | 90.99 weight % |
| Application 3: | |
| green tea leaf extract | 5 weight % |
| sunflower seed extract | 2 weight % |
| beta carotene oil | 0.01 weight % |
| ascorbic acid | 1 weight % |
| α-tocophenol | 0.5 weight % |
| fatty acid ester as dispersing agent | 1 weight % |
| water | 90.49 weight % |

Additionally, active oxygen free radical scavenging food containing the ingredients of application 4 is preferably manufactured.

| Application 4: | |
| --- | --- |
| green tea leaf extract | 15 weight % |
| sunflower seed extract | 15 weight % |
| beta carotene oil | 1 weight % |
| ascorbic acid | 5 weight % |
| sesame powder | 60 weight % |
| lactose | 4 weight % |

The active oxygen free radical scavenging agent of this embodiment is easily mixed with beta carotene, ascorbic acid, α-tocophenol, etc. The mixing does not disturb the active oxygen free radical scavenging effect of the produced drinks and foods of the above applications. Furthermore, as teas and sunflower seeds have been traditionally taken in as foods and drinks, the active oxygen free radical scavenging agent of this embodiment is superior in safety.

INDUSTRIAL APPLICABILITY

As aforementioned, the active oxygen free radical scavenging agent of the present invention includes green tea leaf extract containing epigallo catechin gallate and sunflower seed extract containing chlorogenic acid. These extracts are independently effective in scavenging active oxygen free radicals. However, the mixture of those extracts has better active oxygen free radical scavenging effect. Therefore, the active oxygen free radical scavenging agent of the present invention is effective in scavenging active oxygen free radicals which may cause inflammation, cerebral hemorrhage, arterial sclerosis, generation of cancers, radiation damage, cataract, aging, etc. Furthermore, as teas and sunflower seeds have been traditionally taken in as foods and drinks, the active oxygen free radical scavenging agent of the present invention is superior in safety.

I claim:

1. An active oxygen free radical scavenging agent for organisms, comprising:

a sunflower seed extract having a chlorogenic acid; and a green tea leaf extract having an epigallo catechin gallate.

2. An active oxygen free radical scavenging agent according to claim 1, wherein said green tea extract and said sunflower seed extract are each dispersed in water and used in an amount of between approximately 0.01 weight per cent to 10.00 weight percent.

3. An active oxygen free radical scavenging agent according to claim 1, wherein said scavenging agent includes at least one antioxidant.

4. An active oxygen free radical scavenging agent according to claim 3, wherein said at least one antioxidant is selected from the group comprising ascorbic acid, vitamin E, beta carotene and a fragrance.

5. An active oxygen radical free scavenging agent according to claim 1, wherein said scavenging agent is mixed with at least one of lactose, dextrin and a food material prior to dispensing to an end user.

6. An active oxygen radical free scavenging agent according to claim 2, wherein said scavenging agent is mixed with a food material.

7. A food additive, for an organism, having an active oxygen free radical scavenging agent, said active oxygen free radical scavenging agent comprising:

a sunflower seed extract having a chlorogenic acid;

a green tea leaf extract having an epigallo catechin gallage; and said green tea extract and said sunflower seed extract each being dispersed in water and being used in an amount of between approximately 0.01 weight percent to 10.00 weight percent.

8. An organism active oxygen free radical scavenging agent comprising:

a green tea leaf extract having an epigallo catechin gallate being used in a quantity of about 5 percent by weight;

a sunflower seed extract being used in a quantity of about 2 percent by weight;

beta carotene oil being used in a quantity of about 0.01 percent by weight;

ascorbic acid being used in a quantity of about 1 percent by weight;

α-tocophenol being used in an amount of about 0.5 percent by weight;

a dispersing agent being used in an amount of about 1 percent by weight; and water in being used an amount of about 90.49 percent by weight.

9. An active oxygen free radical scavenging agent according to claim 8, wherein said dispersing agent in a fatty acid ester.

* * * * *